(12) United States Patent
Burkholz et al.

(10) Patent No.: US 11,291,393 B2
(45) Date of Patent: Apr. 5, 2022

(54) MEDICAL DEVICE FOR COLLECTION OF A BIOLOGICAL SAMPLE

(71) Applicant: Becton, Dickinson and Company, Franklin Lakes, NJ (US)

(72) Inventors: Jonathan Karl Burkholz, Salt Lake City, UT (US); Bryan Garret Davis, Sandy, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 402 days.

(21) Appl. No.: 16/280,449

(22) Filed: Feb. 20, 2019

(65) Prior Publication Data

US 2019/0175088 A1 Jun. 13, 2019

Related U.S. Application Data

(63) Continuation of application No. 14/251,672, filed on Apr. 14, 2014, now Pat. No. 10,238,325.
(Continued)

(51) Int. Cl.
*A61B 5/15* (2006.01)
*G01N 33/49* (2006.01)
(Continued)

(52) U.S. Cl.
CPC ...... *A61B 5/150213* (2013.01); *A61B 5/1411* (2013.01); *A61B 5/151* (2013.01);
(Continued)

(58) Field of Classification Search
CPC .......... A61B 5/150213; A61B 5/15003; A61B 5/150022; A61B 5/150221; A61B 5/150412; A61B 5/150442
See application file for complete search history.

(56) References Cited

U.S. PATENT DOCUMENTS 3,322,114 A    5/1967  Portnoy et al.
3,640,393 A *  2/1972  Hurtig .............. A61B 5/150022
                                                  210/321.84
(Continued)

FOREIGN PATENT DOCUMENTS

CN    1382966 A    12/2002
CN    1846603 A    10/2006
(Continued)

*Primary Examiner* — Sean P Dougherty
(74) *Attorney, Agent, or Firm* — The Webb Law Firm

(57) ABSTRACT

A biological fluid sampling device for collecting a blood sample from a separate vascular access device and for ejecting a portion of the collected sample to a point-of-care testing device for analysis is provided. The biological fluid sampling device includes a body enclosing a reservoir. The reservoir has an internal volume sufficient to contain enough blood for use in a diagnostic test. The sampling device further includes: an access lumen extending from a distal end of the body for establishing fluid communication between a separate vascular access device and the reservoir; an outflow lumen also in fluid communication with the reservoir; and a removable vented cap attached to the outflow lumen including a gas permeable vent in gaseous communication between the reservoir and ambient air. In addition, several sample and transfer devices are provided for obtaining a sample from a subject and transferring the sample to a point-of-care testing device.

19 Claims, 13 Drawing Sheets

Related U.S. Application Data

(60) Provisional application No. 61/811,918, filed on Apr. 15, 2013.

(51) Int. Cl.

| | | |
|---|---|---|
| A61B 5/157 | (2006.01) | |
| B01L 3/00 | (2006.01) | |
| A61B 5/151 | (2006.01) | |
| A61M 1/34 | (2006.01) | |
| B04B 7/08 | (2006.01) | |
| G01N 1/28 | (2006.01) | |
| G01N 1/34 | (2006.01) | |
| G01N 1/40 | (2006.01) | |
| A61M 1/36 | (2006.01) | |

(52) U.S. Cl.
CPC .......... *A61B 5/15003* (2013.01); *A61B 5/157* (2013.01); *A61B 5/150022* (2013.01); *A61B 5/15101* (2013.01); *A61B 5/15105* (2013.01); *A61B 5/15144* (2013.01); *A61B 5/15198* (2013.01); *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150442* (2013.01); *A61B 5/150748* (2013.01); *A61B 5/150755* (2013.01); *A61B 5/150778* (2013.01); *A61M 1/34* (2013.01); *A61M 1/3406* (2014.02); *A61M 1/36* (2013.01); *B01L 3/502* (2013.01); *B01L 3/5021* (2013.01); *B01L 3/50273* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150969* (2013.01); *B01L 2200/027* (2013.01); *B01L 2200/0621* (2013.01); *B01L 2200/0631* (2013.01); *B01L 2200/0684* (2013.01); *B01L 2200/10* (2013.01); *B01L 2300/0627* (2013.01); *B01L 2300/0672* (2013.01); *B01L 2300/0681* (2013.01); *B01L 2300/0803* (2013.01); *B01L 2300/0864* (2013.01); *B01L 2300/0877* (2013.01); *B01L 2400/0406* (2013.01); *B01L 2400/0409* (2013.01); *B01L 2400/0478* (2013.01); *B01L 2400/0688* (2013.01); *G01N 2001/4016* (2013.01); *G01N 2001/4088* (2013.01)

(56) References Cited

U.S. PATENT DOCUMENTS

| | | | | |
|---|---|---|---|---|
| 4,134,512 A * | 1/1979 | Nugent | A61B 5/15003 | 215/247 |
| 4,436,098 A * | 3/1984 | Kaufman | A61B 5/1545 | 600/579 |
| 4,511,349 A * | 4/1985 | Nielsen | B01L 3/5021 | 422/533 |
| 4,627,445 A * | 12/1986 | Garcia | A61B 5/14532 | 600/583 |
| 5,055,203 A * | 10/1991 | Columbus | A61B 5/15003 | 210/741 |
| 5,163,442 A * | 11/1992 | Ono | A61B 5/150022 | 600/565 |
| 5,219,999 A * | 6/1993 | Suzuki | C07K 16/00 | 530/390.5 |
| 5,422,018 A * | 6/1995 | Saunders | B01D 21/20 | 210/787 |
| 5,636,640 A * | 6/1997 | Staehlin | A61B 5/150022 | 600/577 |
| 5,726,026 A * | 3/1998 | Wilding | B01D 67/0062 | 366/DIG. 3 |
| 5,839,715 A * | 11/1998 | Leinsing | A61M 39/1011 | 251/149.1 |
| 5,922,591 A * | 7/1999 | Anderson | B01F 13/0059 | 435/287.2 |
| 6,074,183 A * | 6/2000 | Allen | B01D 35/26 | 210/416.1 |
| 6,264,619 B1 * | 7/2001 | Ferguson | A61B 5/15003 | 206/569 |
| 6,506,167 B1 * | 1/2003 | Ishimito | B01L 3/5021 | 600/577 |
| 6,869,405 B2 | 3/2005 | Marsden | | |
| 8,158,410 B2 * | 4/2012 | Tang | G01N 33/491 | 435/288.5 |
| 8,267,911 B2 * | 9/2012 | Gallogly | A61B 5/150992 | 604/408 |
| 8,383,044 B2 | 2/2013 | Davis et al. | | |
| 8,491,499 B2 * | 7/2013 | Choi | A61B 5/15142 | 600/576 |
| 9,028,425 B2 * | 5/2015 | Burkholz | A61B 5/150221 | 600/577 |
| 9,549,701 B2 * | 1/2017 | Peterson | A61B 5/15003 | |
| 2002/0009015 A1 * | 1/2002 | Laugharn, Jr. | B01J 19/10 | 366/108 |
| 2002/0143298 A1 * | 10/2002 | Marsden | G01N 1/14 | 604/190 |
| 2003/0134416 A1 * | 7/2003 | Yamanishi | A61M 1/36 | 435/372 |
| 2004/0116830 A1 * | 6/2004 | Trudeau | A61B 5/14539 | 600/584 |
| 2004/0142463 A1 * | 7/2004 | Walker | A61M 1/3679 | 435/325 |
| 2004/0143226 A1 * | 7/2004 | Marsden | A61B 5/150572 | 604/272 |
| 2004/0230216 A1 * | 11/2004 | Levaughn | A61B 5/150725 | 606/181 |
| 2005/0069459 A1 * | 3/2005 | Ahn | B01L 3/502753 | 422/504 |
| 2005/0214927 A1 * | 9/2005 | Haley | C12M 47/02 | 435/283.1 |
| 2005/0273019 A1 * | 12/2005 | Conway | A61B 5/15074 | 600/576 |
| 2006/0009713 A1 * | 1/2006 | Flaherty | A61B 5/150213 | 600/576 |
| 2006/0029923 A1 * | 2/2006 | Togawa | B01D 61/18 | 435/2 |
| 2006/0229530 A1 * | 10/2006 | Hosoda | A61B 5/150343 | 600/573 |
| 2006/0240964 A1 * | 10/2006 | Lolachi | A61M 1/3693 | 494/37 |
| 2007/0031283 A1 * | 2/2007 | Davis | A61B 5/150221 | 422/400 |
| 2007/0160503 A1 * | 7/2007 | Sethu | B03C 5/024 | 422/400 |
| 2008/0097315 A1 * | 4/2008 | Miner | A61M 5/1411 | 604/122 |
| 2008/0135502 A1 * | 6/2008 | Pyo | B01D 21/0075 | 210/801 |
| 2008/0240990 A1 * | 10/2008 | Flaherty | A61B 5/15003 | 422/68.1 |
| 2008/0287906 A1 * | 11/2008 | Burkholz | A61M 25/0693 | 604/500 |
| 2009/0004060 A1 * | 1/2009 | Omuro | A61B 5/150022 | 422/73 |
| 2009/0136982 A1 * | 5/2009 | Tang | G01N 1/40 | 435/29 |
| 2009/0181411 A1 * | 7/2009 | Battrell | B01F 11/0074 | 435/7.92 |
| 2009/0204026 A1 * | 8/2009 | Crawford | A61B 5/1444 | 600/576 |
| 2010/0089815 A1 * | 4/2010 | Zhang | B01L 3/502753 | 210/335 |

(56) References Cited

U.S. PATENT DOCUMENTS

| | | | | |
|---|---|---|---|---|
| 2010/0093551 | A1* | 4/2010 | Montagu | G01N 33/491 506/7 |
| 2010/0198108 | A1* | 8/2010 | Alden | A61B 5/150358 600/583 |
| 2010/0241031 | A1* | 9/2010 | Lai | A61B 5/150412 600/583 |
| 2011/0009717 | A1* | 1/2011 | Davis | A61B 5/150389 600/309 |
| 2011/0124130 | A1* | 5/2011 | Wagner | G01N 33/558 436/518 |
| 2011/0124984 | A1* | 5/2011 | Rostaing | A61B 5/150969 600/309 |
| 2012/0016213 | A1* | 1/2012 | Burkholz | A61B 5/150251 600/309 |
| 2012/0152858 | A1* | 6/2012 | Yang | B01L 3/502761 210/767 |
| 2012/0275955 | A1* | 11/2012 | Haghgooie | A61B 5/154 422/44 |
| 2012/0277696 | A1* | 11/2012 | Gonzalez-Zugasti | A61B 5/15144 604/318 |
| 2012/0277697 | A1* | 11/2012 | Haghgooie | A61B 10/0045 604/319 |
| 2013/0026085 | A1* | 1/2013 | Samsoondar | B01D 63/02 210/136 |
| 2013/0052675 | A1* | 2/2013 | Karlsson | G01N 33/721 435/15 |
| 2013/0082012 | A1* | 4/2013 | Lean | B01D 21/02 210/804 |
| 2013/0086980 | A1* | 4/2013 | Gadini | C12M 47/02 73/61.71 |
| 2013/0165867 | A1* | 6/2013 | Isaacson | A61M 39/0606 604/256 |
| 2013/0175213 | A1* | 7/2013 | Dorrer | B01D 63/088 210/435 |
| 2013/0209331 | A1* | 8/2013 | Rodenfels | G01N 33/491 422/534 |

FOREIGN PATENT DOCUMENTS

| | | |
|---|---|---|
| CN | 101102847 A | 1/2008 |
| CN | 101317758 A | 12/2008 |
| CN | 101332320 A | 12/2008 |
| CN | 101600963 A | 12/2009 |
| CN | 101695446 A | 4/2010 |
| CN | 102573629 A | 7/2012 |
| CN | 102764133 A | 11/2012 |
| CN | 202844313 U | 4/2013 |
| DE | 202008010918 U1 | 1/2009 |
| EP | 0376168 A2 | 7/1990 |
| EP | 0747105 A2 | 12/1996 |
| EP | 1096254 A2 | 5/2001 |
| EP | 1106065 A2 | 6/2001 |
| EP | 1477804 A1 | 11/2004 |
| EP | 1602329 A1 | 12/2005 |
| EP | 1627651 A2 | 2/2006 |
| EP | 2264453 A1 | 12/2010 |
| EP | 2413138 A2 | 12/2010 |
| FR | 2929135 A1 | 2/2012 |
| FR | 2977808 A1 | 1/2013 |
| JP | 544191 | 1/1979 |
| JP | 4276258 A | 10/1992 |
| JP | 2004361419 A | 12/2004 |
| JP | 2005287955 A | 10/2005 |
| JP | 2005349195 A | 12/2005 |
| JP | 201155916 A | 3/2011 |
| JP | 2012532683 A | 12/2012 |
| WO | 9309710 A1 | 5/1993 |
| WO | 2005018710 A2 | 3/2005 |
| WO | 2006047831 A1 | 5/2006 |
| WO | 2007002579 A2 | 1/2007 |
| WO | 2009123592 A1 | 10/2009 |
| WO | 2011040874 A1 | 4/2011 |
| WO | 2012121686 A1 | 9/2012 |

* cited by examiner

MEDICAL DEVICE FOR COLLECTION OF A BIOLOGICAL SAMPLE

CROSS-REFERENCE TO RELATED APPLICATION

The present application is a continuation of U.S. patent application Ser. No. 14/251,672, filed Apr. 14, 2014, entitled "Medical Device for Collection of a Biological Sample", which claims priority to U.S. Provisional Application No. 61/811,918, filed Apr. 15, 2013, entitled "Medical Device for Collection of a Biological Sample", the entire disclosures of each of which are hereby incorporated by reference.

BACKGROUND OF THE INVENTION

1. Field of the Invention

The present invention relates to devices, assemblies, and systems adapted for use with vascular access devices, for collecting biological samples for use in point-of-care testing, and for filling specimen collection containers for use in conventional laboratory testing.

2. Description of Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Once collected, blood samples may be analyzed to obtain medically useful information including chemical composition, hematology, coagulation, etc.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process. A simplified device for providing blood for point-of-care testing is, therefore, desired. Additionally, since point-of-care tests are often supplemented with further conventional laboratory testing, it is also desirable to have a blood sampling and collection assembly that can be used to collect a blood sample for traditional laboratory testing and a second sample for point-of-care testing. These features are accomplished through the device, assembly, and system of the present invention.

SUMMARY OF THE INVENTION

In view of the above-described shortcomings within the prior art, a biological fluid sampling device for point-of-care testing, an extravascular system for collecting fluid samples, and methods of use thereof are provided herein. Further details and advantages of the present invention will be understood from the following detailed description read in conjunction with the accompanying drawings.

In accordance with an embodiment of the present invention, a biological fluid sampling device, such as a blood sampling device, includes a housing enclosing a biological fluid reservoir defining an interior, and an access lumen extending from a portion of the housing and establishing fluid communication between the separate vascular access device and the interior of the reservoir. The device also includes an outflow lumen extending from a portion of the housing, with the outflow lumen having a first end provided in fluid communication with the interior of the reservoir and a second end. The device also includes a vented cap removably disposed over the second end of the outflow lumen, the vented cap comprising a gas permeable vent in gaseous communication between the interior of the reservoir and an ambient environment.

In certain configurations, the device also includes a luer lock at least partially surrounding the access lumen. The vented cap may include a luer lock for insertion in the outflow lumen. The vented cap may also include a fastener for removably connecting a portion of the cap to a portion of the housing. The interior of the reservoir may be configured for receiving a fluid sample therein. The housing may also include a compressible portion and compression of the compressible portion may expel a fluid sample from the interior of the reservoir through the access lumen.

In certain configurations, the access lumen is disposed at a distal end of the housing and the outflow lumen is disposed at a proximal end of the housing. The reservoir may also contain a sample stabilizer. In still other configurations, the housing may have a visual identifier which corresponds to a specific sample stabilizer. The visual identifier may be a specific color. Optionally, the vent may include at least one of a porous plug, a permeable membrane, and small vent holes.

In accordance with another embodiment of the present invention, a biological fluid sampling and collection assembly, such as a blood sampling and collection assembly, may include a biological fluid sampling device. The biological fluid sampling device includes a housing enclosing a biological fluid reservoir defining an interior, and an access lumen extending from a portion of the housing and establishing fluid communication between a separate vascular access device and the interior of the reservoir. The device may also include an outflow lumen extending from a portion of the housing, with the outflow lumen having a first end provided in fluid communication with the interior of the reservoir and a second end. The assembly may also include a sample collection device including an adapter for accessing an interior of a sample container and for establishing fluid communication between the biological fluid reservoir and an interior of the sample container. This allows fluid communication between the interior of the reservoir and the interior of the sample container. The sample collection device may also include a flow restrictor engaged with the adapter. The flow restrictor may be transitionable from an open position, in which fluid communication is permitted between the biological fluid reservoir and the interior of the sample container, to a closed position, in which the biological fluid reservoir is in fluid isolation from the interior of the sample container.

In certain configurations, the biological fluid reservoir contains a fluid and when the flow restrictor is in the open position, the fluid passes from the biological fluid reservoir to the interior of the sample container. The flow restrictor is in the open position when the sample container is engaged with the adapter, and the flow restrictor is in the closed position when the sample container is removed from the adapter.

In other configurations, the assembly further includes a vented cap removably disposed over the second end of the outflow lumen. The vented cap includes a gas permeable vent in gaseous communication between the interior of the reservoir and an ambient environment. The sample container may be a vacuum evacuated container. The assembly may further include the separate vascular access device in fluid communication with the access lumen.

In still other configurations, the assembly includes an adapter connected between the separate vascular access device and the biological sampling device. The adapter may include a housing, a main lumen enclosed within the housing having a main outflow port, a side port including a side lumen extending from and in fluid communication with the main lumen, and a valve transitionable from a first position in which fluid flow is permitted through the main lumen and fluid flow is prevented through the side lumen, to a second position in which fluid flow through both the main lumen and side lumen is permitted. The valve may be transitioned from the first position to the second position by insertion of a tubular member into the side lumen through the side port.

BRIEF DESCRIPTION OF THE DRAWINGS

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

DETAILED DESCRIPTION OF THE EMBODIMENTS

Figure 1:
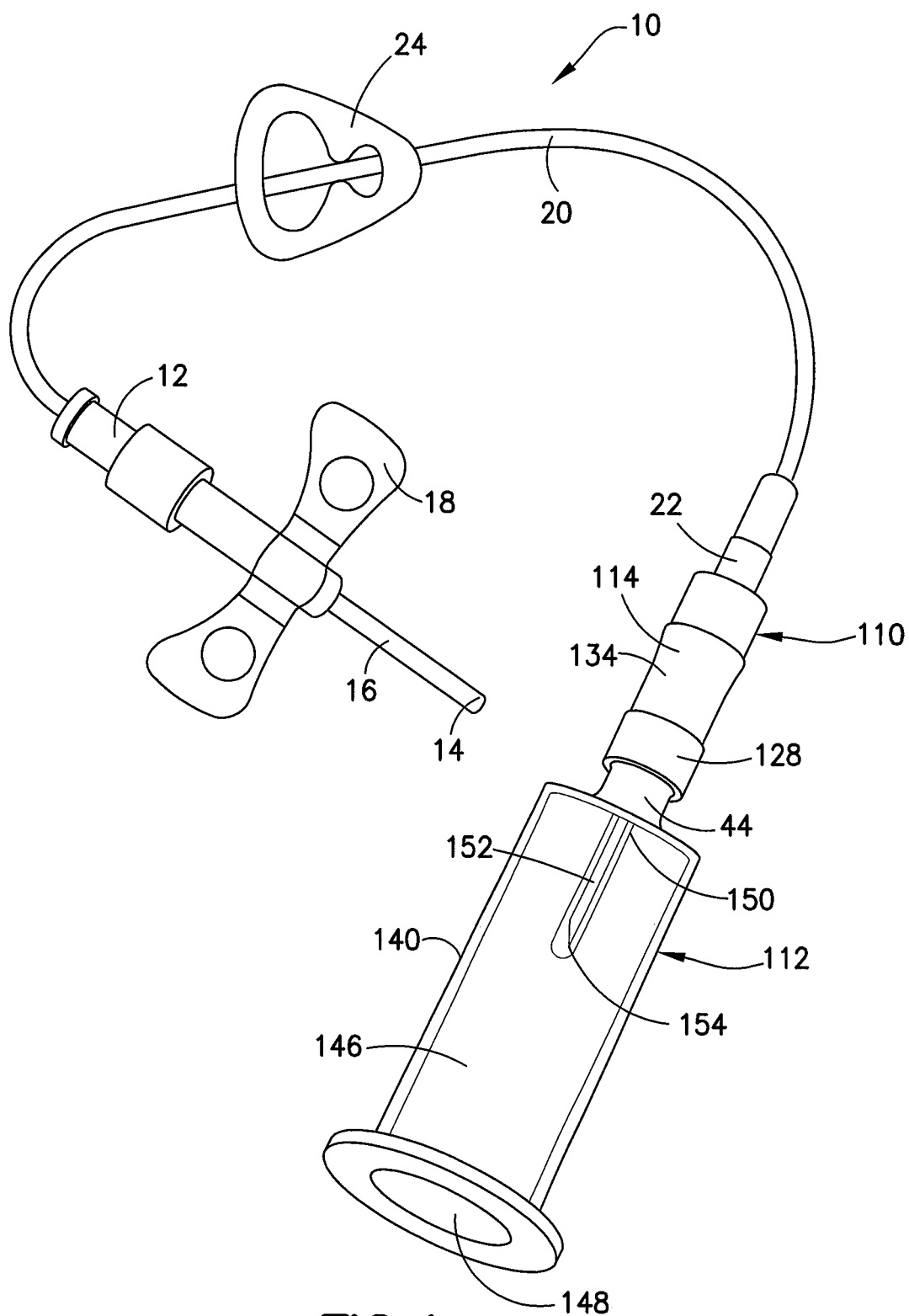
FIG. 1 is a perspective view of a biological fluid sampling device, a sample container collection device, and a separate vascular access device in accordance with an embodiment of the present invention.

For the purpose of facilitating understanding of the invention, the accompanying drawings and description illustrate preferred embodiments thereof, from which the invention, various embodiments of its structures, construction and method of operation, and many advantages may be understood and appreciated.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present invention relates to a biological fluid sampling device, such as a blood sampling device 110, used to collect a blood sample for use in point-of-care testing and analysis. The blood sampling device 110 is configured as part of a larger extravascular system 10, and is configured to receive the fluid sample from a separate vascular access device 12. An exemplary extravascular system is depicted in FIG. 1. The system includes the blood sampling device 110, a sample container collection device 112, and the vascular access device 12. The vascular access device 12 may include numerous components such as an intravascular needle 14, an over-the-needle catheter 16, and needle shielding structure 18, as well as integrated extension tubing 20 terminating in a luer access adapter 22 or port, as is known in the art.

Exemplary vascular access devices include both straight and ported intravenous catheters such as the AUTO-GUARD™ shielded catheter commercially available from Becton, Dickinson, and Company, integrated peripheral intravenous catheters, winged needle sets, and blood collections sets. An IV access set, such as the BD NEXIVA™ Closed Intravenous (IV) Catheter System commercially available from Becton, Dickinson, and Company may also be used to create a closed access system. Similarly, an enclosed luer adapter port such as the BD Q-SYTE™ Luer Access Split Septum, also commercially available from Becton, Dickinson, and Company, may be used to entirely enclose the luer access adapter 22 between the sampling device 110 and vascular access device 12. Alternatively, the sampling device 110 may be directly connected to an intravenous catheter hub, without additional components such as extension tubing 20, to reduce the number of components and simplify the collection and sampling process.

Figure 8:
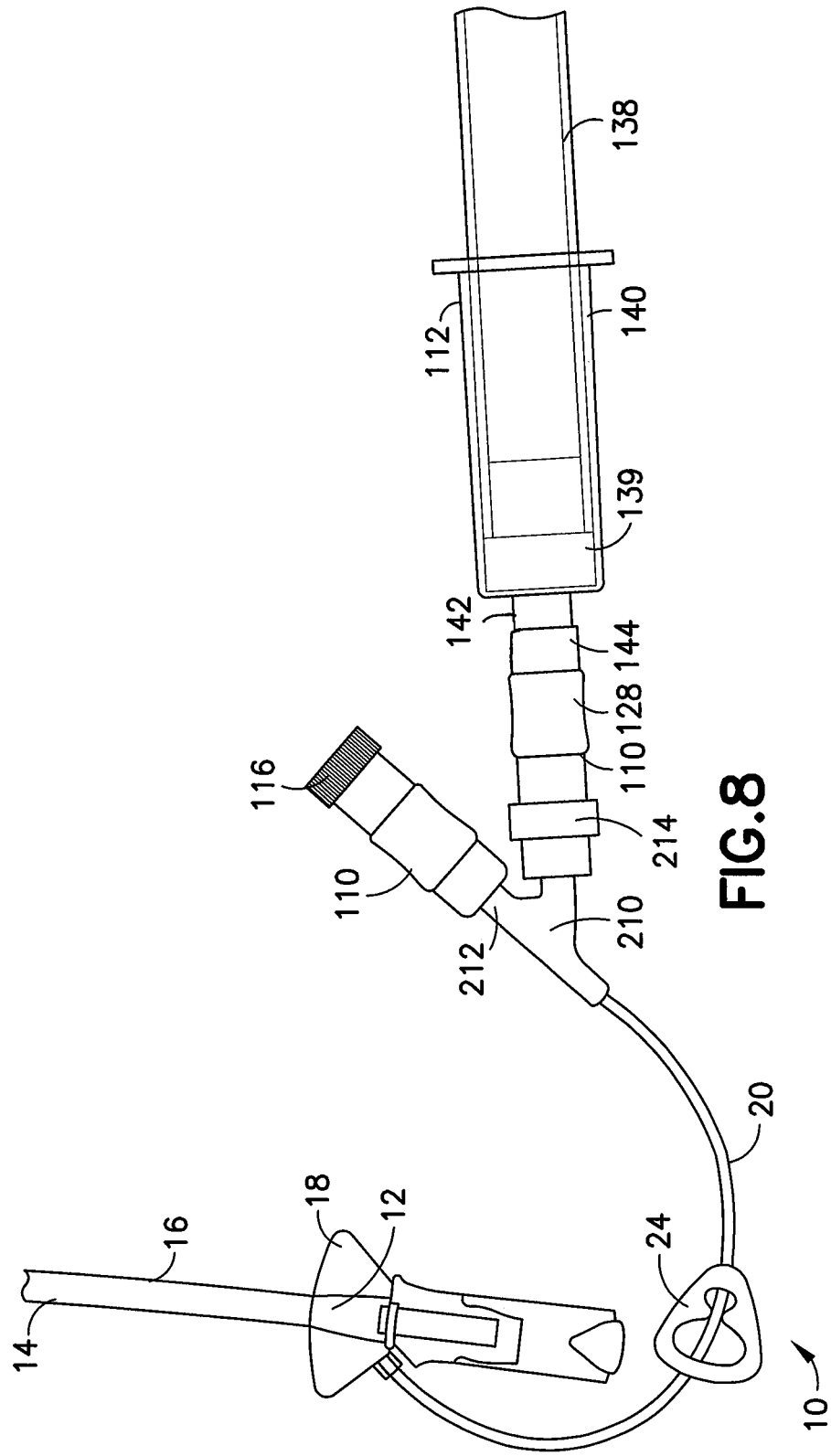
FIG. 8 is a perspective view of a system including a biological fluid sampling device, a sample container collection device, a side port connector, and a separate vascular access device in accordance with an embodiment of the present invention
Figure 13:
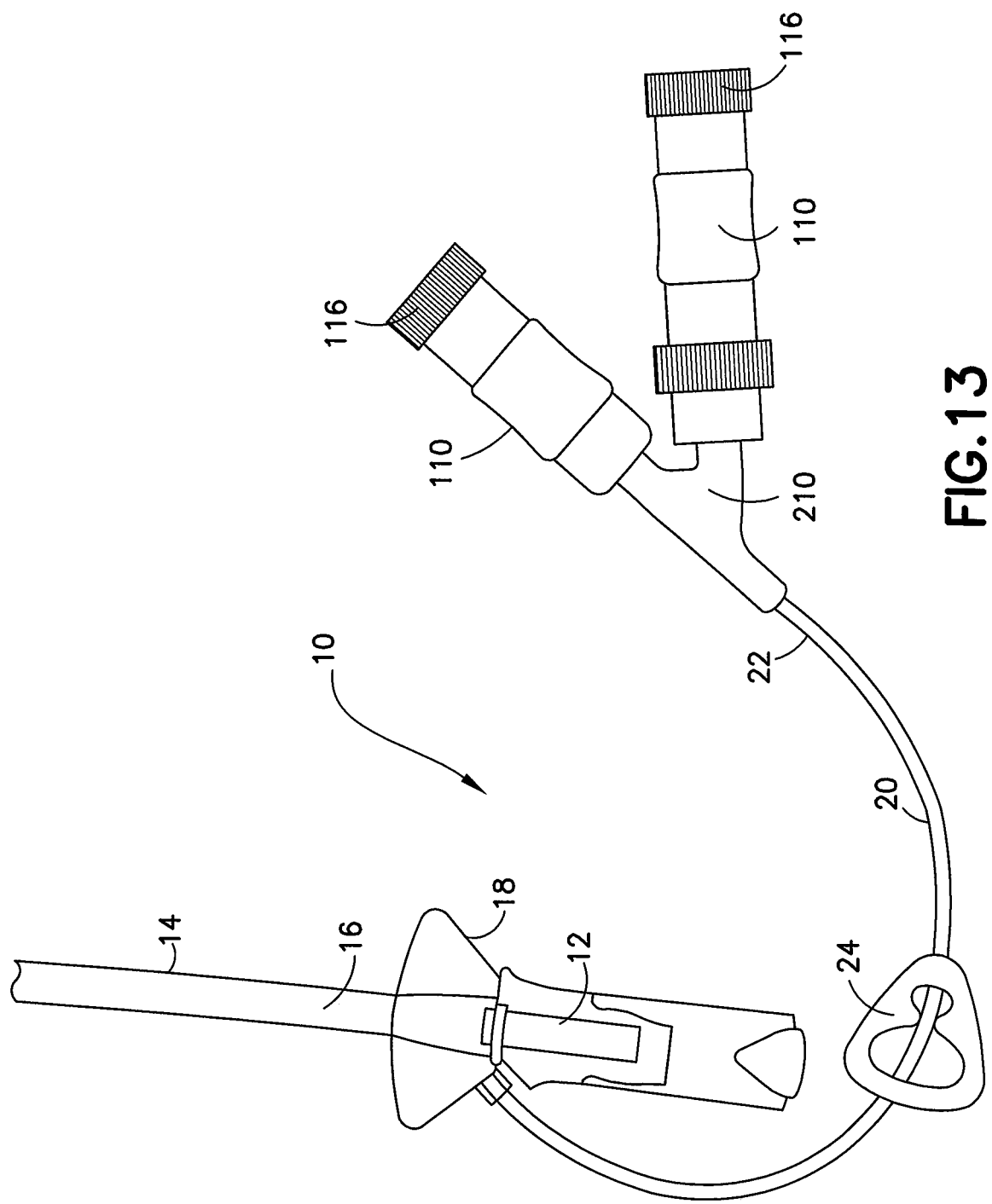
FIG. 13 is a perspective view of a system including two biological fluid sampling devices, a side port connector, and a separate vascular access device connected to the side port device in accordance with an embodiment of the present invention.

The vascular access device 12 may further include a flow restrictor, such as a clamp 24, to restrict blood flow through the extension tubing 20 when the sampling device 110 and/or collection device 112 are removed from the extravascular system 10. Alternatively, the luer access adapter 22 may include an integral valve or septum which automatically closes to restrict fluid flow after the sampling device 110 is removed from the extravascular system 10. As will be described in greater detail below, the present invention is intended to include various modular components which can be combined to form numerous extravascular systems based on the types of blood samples to be collected. It is also intended herein, that an integrated unit of both the luer access adapter 22 and the sampling device 110 may be provided within the scope of the present invention. Alternative configurations of an extravascular system 10, within the scope of the present invention and including multiple blood sampling devices and/or specimen container collection devices, are depicted in FIGS. 8 and 13.

Figure 2:
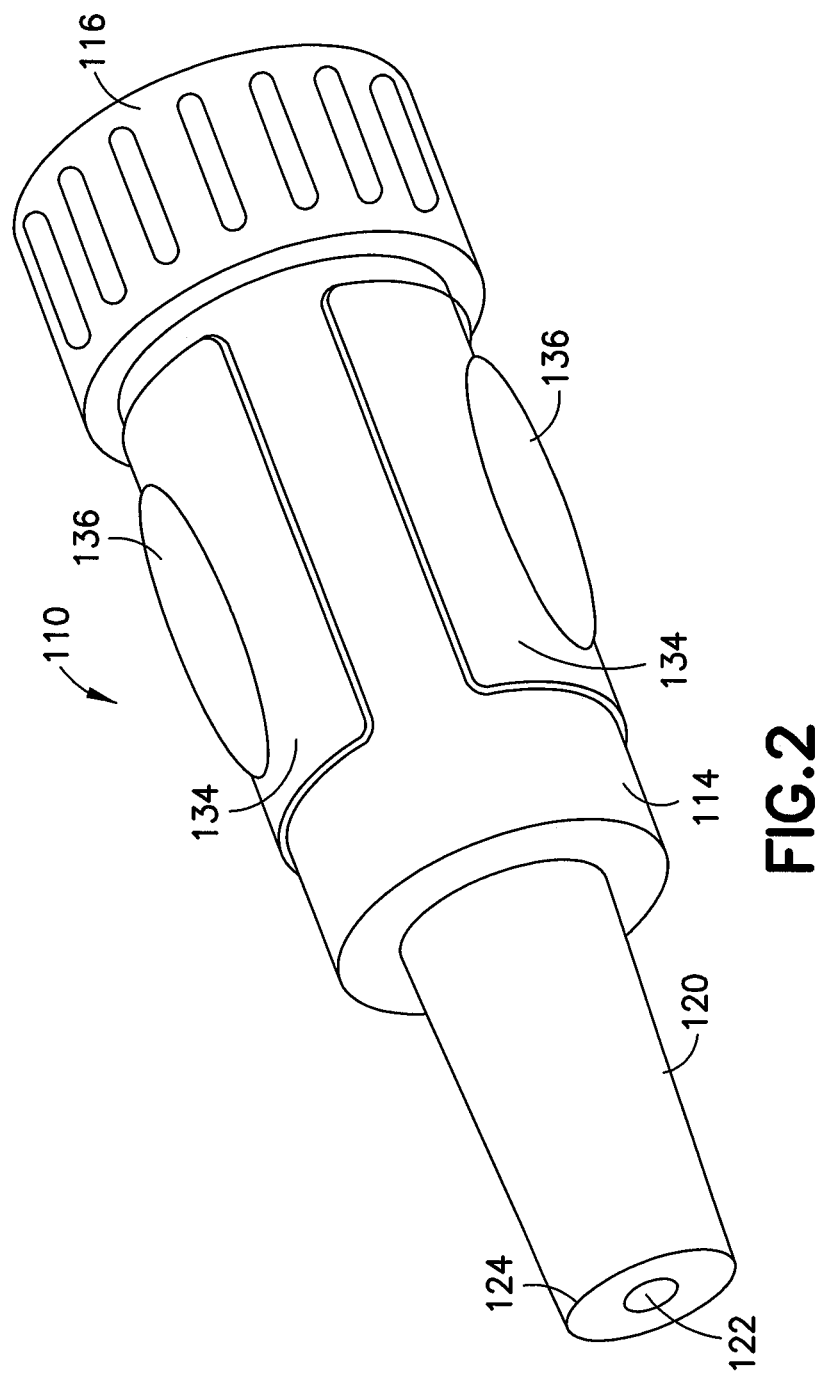
FIG. 2 is a perspective view of the biological fluid sampling device of FIG. 1 including a vented cap.

The blood sampling device 110 includes a housing body 114, which may be formed by injection molding or blow molding, and a removeable vented end cap 116 as shown in FIG. 2. The blood sampling device 110 can, in some cases, reduce the number of components required to draw a diagnostic blood sample from a patient. This is because the blood sampling device 110 combines the ability to perform the processes of venting the extravascular system and obtaining a blood sample into a single device. More specifically, the blood sampling device 110 is configured to vent air from the extravascular system 10, thereby drawing blood from the vascular access device 12 through extension tubing 20 to the sampling device 110. External power sources such as motorized pumps, as are known in the art, may also be used to push blood through the extravascular system 10 to the sampling device 110. The blood sampling device 110 may also receive blood via a wicking means disposed within a distal end of the device, for drawing blood into the device. The blood is retained within a reservoir 118, as shown in FIG. 4, of the sampling device 110.

Once the blood sampling device 110 is removed from the extravascular system 10, blood may be expelled from the sampling device 110, as described in greater detail below, to a point-of-care testing device 30 (shown in FIG. 14) such as a test strip, glass slide, diagnostic cartridge, or other testing device for testing and analysis. Test strips, glass slides, and diagnostic cartridges are point-of-care testing devices that receive a blood sample and test that blood for one or more physiological and biochemical states. Examples of testing cartridges include the i-STAT® testing cartridge commercially available from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

Figure 3:
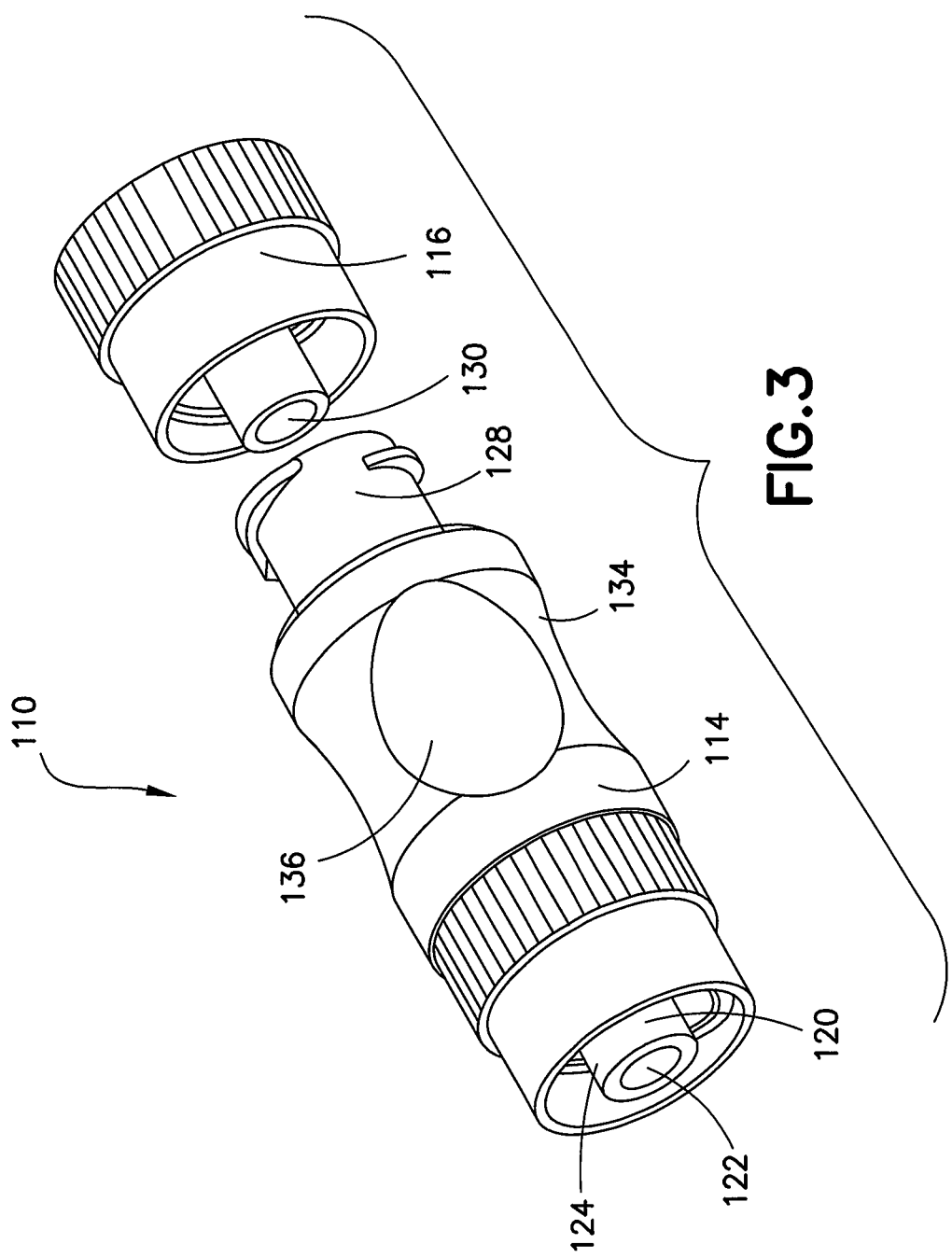
FIG. 3 is a perspective view of the biological fluid sampling device of FIG. 1 with a vented cap detached from the body of the device.
Figure 4:
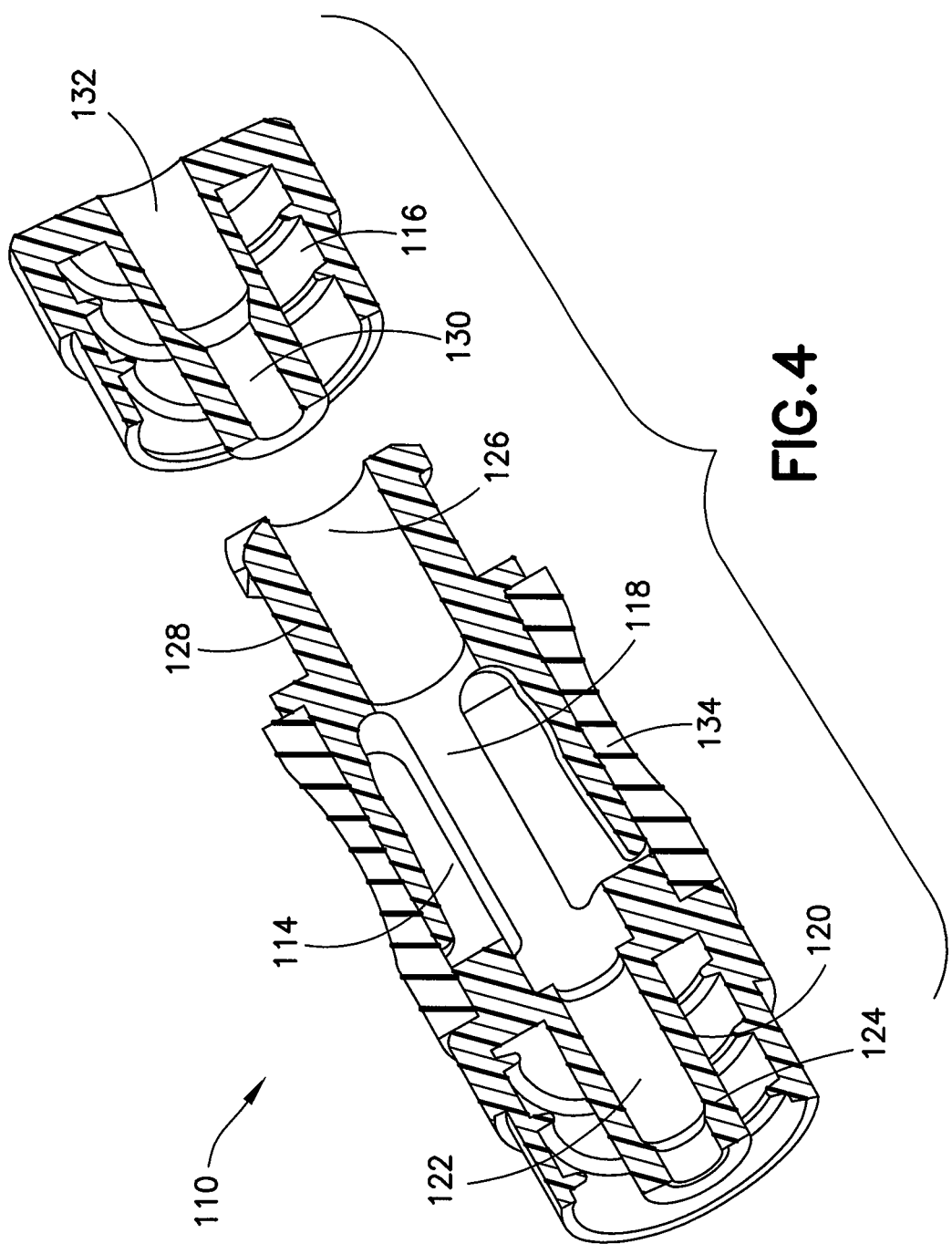
FIG. 4 is a perspective cross-sectional view of the biological fluid sampling device of FIG. 1 with the vented cap detached from the body of the device.

With reference to FIGS. 2-4, the structure of the biological sampling device will now be described in greater detail. The housing body 114 of the biological sampling device 110 includes a narrow tubular portion 120 having an access lumen 122 configured to establish fluid communication with the separate vascular access device 12. For example, the narrow tubular portion 120 may be a male luer lock connection 124 adapted for insertion into the female luer access adapter 22 of the vascular access device 12. The reservoir 118 is enclosed within the housing body 114 and includes an internal volume sufficient to contain enough blood for use in a diagnostic test, for example, an internal volume of between about 0.1 mL and about 10 mL. Because different blood tests require different quantities of blood, in some embodiments, the reservoir 118 is sized to retain a quantity of blood needed for a specific test or a specific number of tests. The reservoir 118 may be provided with various sample stabilizers, such as blood preservatives, reagents, or anti-coagulants (e.g., heparin) to maintain the blood and to ensure its usefulness for certain intended blood tests. Optionally, the housing body 114 of the blood sampling device 110 may be provided as a specific color to signal to a user that the reservoir 118 of the sampling device 110 includes the blood preserving chemical. Blood sampling devices without the preservative may have a different housing body color to signal to the user that the blood sampling device does not include such chemicals.

The reservoir 118 is in fluid communication with both the access lumen 122 and an outflow lumen 126, generally disposed on an opposite end of the housing body 114 from the access lumen 122. The outflow lumen 126 may be enclosed by a connection structure such as a threaded port 128. As shown in the embodiments depicted in FIGS. 2-4, the threaded port 128 and outflow lumen 126 are connected to the removable end cap 116.

The removable cap 116 is configured to be attached to the threaded port 128 and includes an inner channel 130 extending through a portion of the end cap 116 which is in fluid communication with the outflow lumen 126 and reservoir 118. The inner channel 130 is provided with a gas permeable vent 132 which permits gas to pass therethrough but which prevents passage of a fluid such as blood. The vent 132 may include various structures capable of providing these properties, such as porous plugs, permeable membranes, and/or structures containing a plurality of small venting holes. The vent 132 may include a permeable portion formed from a combination of glass, polyethylene terephthalate (PET), microfiber material, and/or other synthetic materials made of high-density polyethylene fibers. The vent 132 may be hydrophobic or hydrophilic. Optionally, the vent 132 may include layers of different materials to enable the vent 132 to be both hydrophobic and air permeable.

After a sufficient portion of blood for testing is collected in the sampling device 110, the sampling device 110 may be removed from the extravascular system 10. In certain configurations of the extravascular system 10 as depicted in FIG. 1, a clamp 24 may be closed to restrict further blood flow through the extension tubing 20 before removing the sampling device 110. Alternatively, the extravascular system 10 may include a valve or septum for automatically restricting fluid flow from the vascular access device 12 once the sampling device 110 is removed.

Once removed from the extravascular system 10, the blood sampling device 110 is configured to eject at least a portion of the collected blood sample from the reservoir 118. For example, in a preferred and non-limiting embodiment, the blood sampling device 110 includes a compressible portion 134. In certain embodiments, the housing body 114 is formed from a flexible or semi-flexible material such that the entire housing body 114 is compressible. Alternatively, the compressible portion 134 may only include a smaller section of the housing body 114 which flexes when pressed. The compressible portion 134 may include ridges or other gripping members 136 to facilitate gripping, holding, and manipulation by a user. In a further non-limiting embodiment, the compressible portion 134 is disposed between two substantially rigid sections, such that the compressible portion 134 compresses when the rigid sections are pressed by a user. In this configuration, the rigid portions provide structural strength and stability for the sampling device 110. The compressible portion 134 of the housing body 114 may be achieved by thinning the wall of the housing body 114 to increase flexibility. Alternatively, the housing body 114 may be formed by a two-shot molding technique in which a flexible material is overmolded around a distal section of the housing body 114. In either case, the compressible portion 134 is more flexible than the rigid sections and configured to deflect inwardly toward the reservoir 118.

In certain configurations, the sampling device 110 is configured to retain blood when uncompressed and to eject an amount of blood when compressed. As such, once removed from the extravascular system 10, blood is naturally retained within the reservoir 118 of the blood sampling device 110 until the compressible portion 134 is compressed by a clinician. When in the uncompressed position, blood is retained within the reservoir 118 by the combination of the surface tension of the blood against the perimeter of the access lumen 122 and the fluid pressure within the reservoir 118. Accordingly, the longitudinal length of the tubular portion 120 and perimeter distance of the access lumen 122 are chosen so that when pressure is within a certain range, blood is retained within the reservoir 118. When the internal volume of the reservoir 118 is reduced, the pressure is increased beyond the retention range and blood is permitted to flow from the sampling device 110 through the access lumen 122. The blood can be ejected to a point-of-care testing device 30, such as a blood test strip, diagnostic cartridge, or onto another type of blood testing/analysis device.

In certain embodiments of the sampling device 110, the sampling device 110 may include multiple chambers within the reservoir 118. Each chamber may have an individual corresponding compressible portion 134 for dispensing only the fluid contained in the respective chamber. In this way, the sampling device 110 may contain individual samples useful for different types of testing. For example, the chambers may have different volumes as needed for particular tests. Additionally, some chambers may include chemicals, blood preservatives, or specific reagents for specific testing needs.

It is also noted that while the sampling device 110 is still connected to the extravascular system 10, the compressible portion 134 of the sampling device 110 may be used to assist in drawing blood from the vascular access device 12 into the reservoir 118. For example, a user may "pump" the compressible portion 134 of the sampling device 110 to assist in pulling the blood sample into the reservoir 118.

Figure 5:
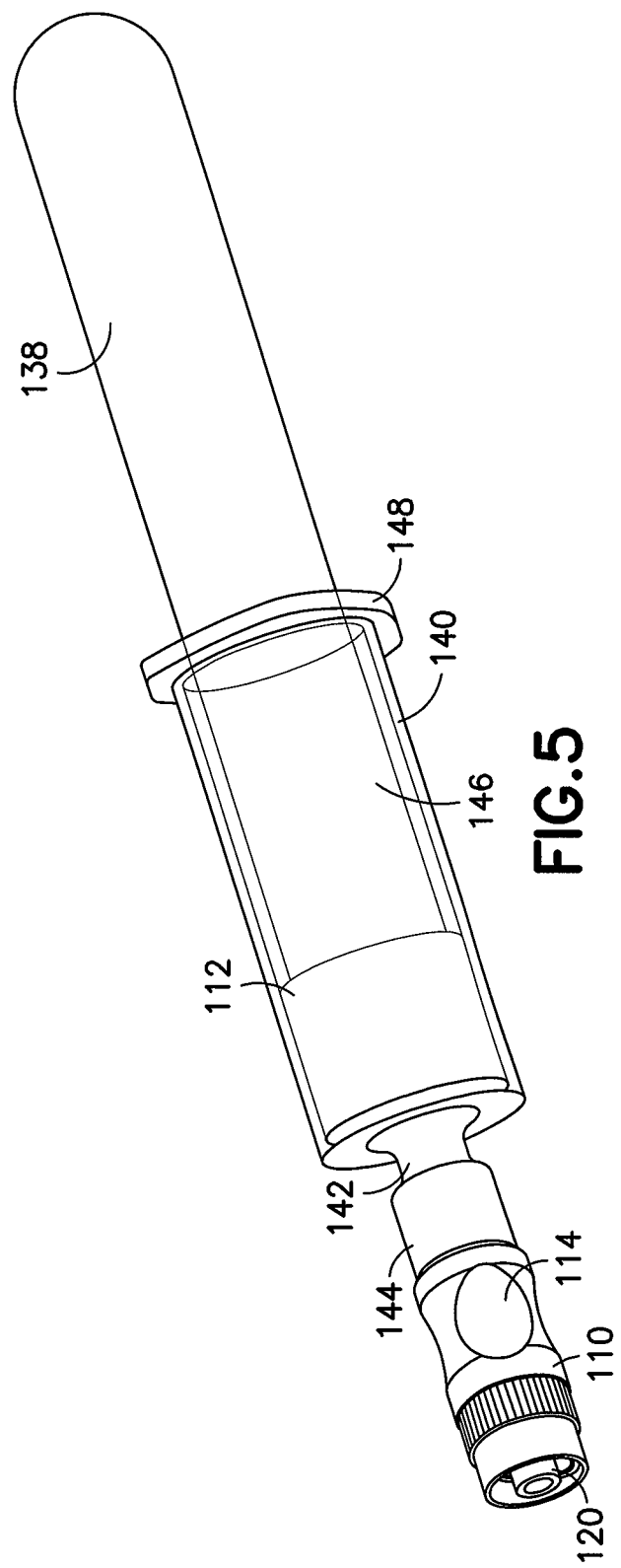
FIG. 5 is a perspective view of an assembly including the biological fluid sampling device and specimen container collection device including a specimen collection container in accordance with an embodiment of the present invention.
Figure 6:
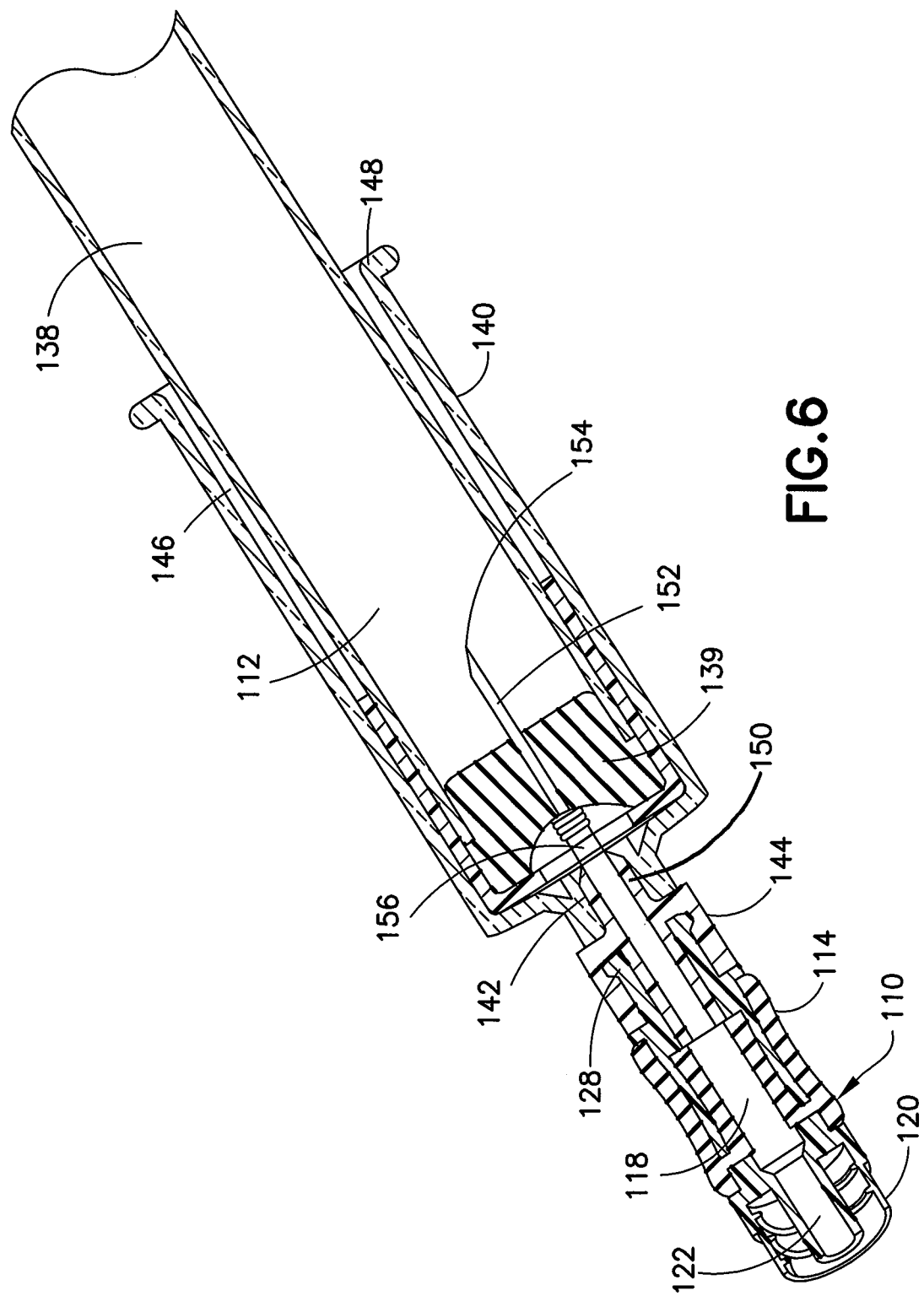
FIG. 6 is a cross-sectional perspective view of the assembly of FIG. 5.
Figure 7:
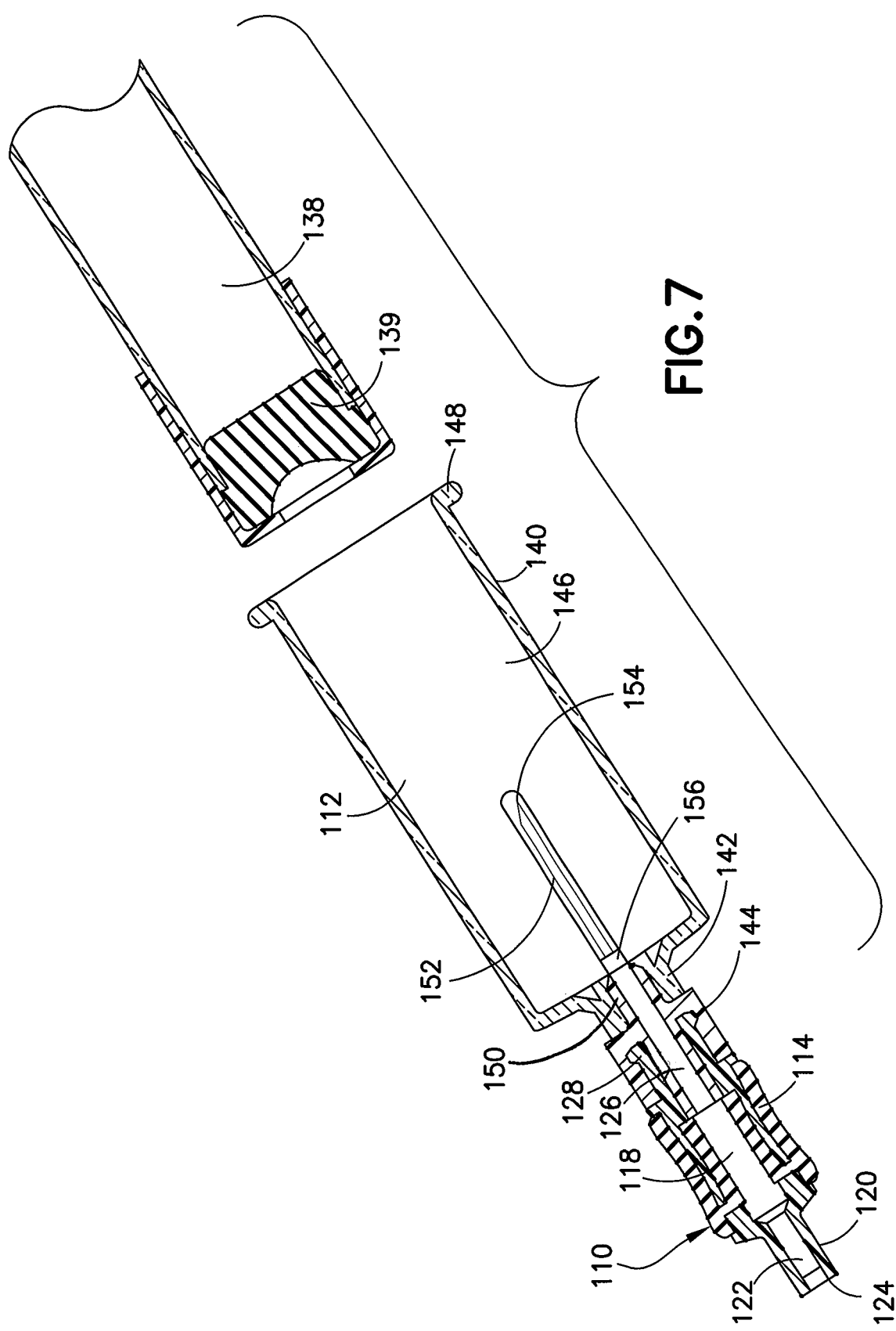
FIG. 7 is a cross-sectional perspective view of the assembly of FIG. 5 with the sample collection container removed from the assembly.

With reference to FIGS. 5-7, in certain configurations, the removable end cap 116 of the blood sampling device 110 is removed and the sampling device 110 is instead connected to the sample container collection device 112 through the threaded port 128 and outflow lumen 126. The sample container collection device 112 may be a vacuum tube collection system (e.g., a Vacutainer). A sample container 138 may be a vacuum evacuated test tube having a pierceable closure or other suitable medical container, as is known in the art. The sample container collection device 112 is configured to establish fluid communication between the separate vascular access device 12 and the sample container 138 through the sampling device 110 so that the sample container 138 may be filled with a blood sample. It is noted, that when the container is a vacuum evacuated tube, the pressure difference between the interior of the tube and the extravascular system 10 can assist in drawing fluid through the extravascular system 10 and into the sample container 138. The filled sample container 138 may be sent to a clinical laboratory for performing certain blood tests as is commonly done in the healthcare industry.

The sample container collection device 112 includes a generally cylindrical body 140 having a fastener 142 for connecting the collection device 112 to the body of the sampling device 110. For example, the collection device 112 may be configured to attach to the threaded port 128 of the sampling device 110 through a corresponding threaded cap 144. The cylindrical body 140 defines an interior region 146 having an open end 148 which receives the sample container 138. A filling adapter 150 extends within the interior region 146 from the threaded cap 144, positioned at the base of the collection device 112, into the interior region 146. The filling adapter 150 may include an elongated needle cannula 152 having a sharpened tip 154 for piercing a closure 139 of the sample container 138.

The collection device 112 is configured such that the sample container 138 is inserted through the open end 148 of the interior region 146, closure 139 side first, and brought into contact with the needle tip 154 of the filling adapter 150. The tip 154 of the needle cannula 152 may be permitted to pierce the closure 139 to access an interior volume of the sample container 138. In this way, blood is permitted to flow from the vascular access device 12, through the sampling device 110, and through the filling adapter 150 into the internal volume of the sample container 138, thereby filling the sample collection container 138.

In certain configurations, a flow restrictor such as a septum 156 is disposed within a lumen of the filling adapter 150. When the sample container 138 is affixed to the collection device 112, the septum 156 is transitioned to the open position to permit fluid to pass therethrough for filling the sample container 138. When the sample container 138 is removed, the septum 156 is permitted to transition to the closed position, thereby blocking fluid access through the needle cannula 152. It is noted that the septum 156 functions in a similar manner to the vented end cap 116 of the embodiment of the sampling device 110 described above. More specifically, when the septum 156 is in the open position, with an evacuate tube connected to the device, air is allowed to vent from the system into the vacuum tube or sample collection container such that air within the extravascular system 10 is vented from the extravascular system 10 through the needle cannula 152. When the valve 156 is in the closed position, fluid flow and air is restricted, thereby preventing air from vacating the system and blood from filing the sampling device. Essentially, when the adapter 150 is connected with a blood sampling device, the blood sampling device is filled with blood via a vacuum tube upon connection with the adapter.

Once a sufficient portion of blood is retained within the reservoir 118, the sampling device 110 and connected collection device 112 can be removed from the extravascular system 10. Blood can be ejected through the access lumen 122 of the sampling device 110 for testing and analysis according to the process described above. As was the case with the biological sampling device 110 described above, the reservoir 118 and access lumen 122 are configured to retain blood within a predetermined fluid pressure range. When the compressible portion of the sampling device 110 is deflected inwardly toward the reservoir 118, the pressure within the reservoir 118 is increased, thereby causing the fluid to be ejected from the sampling device 110 through the access lumen 122. The blood is prevented from being ejected through the outflow lumen 126 by the closed septum 156.

Figure 9:
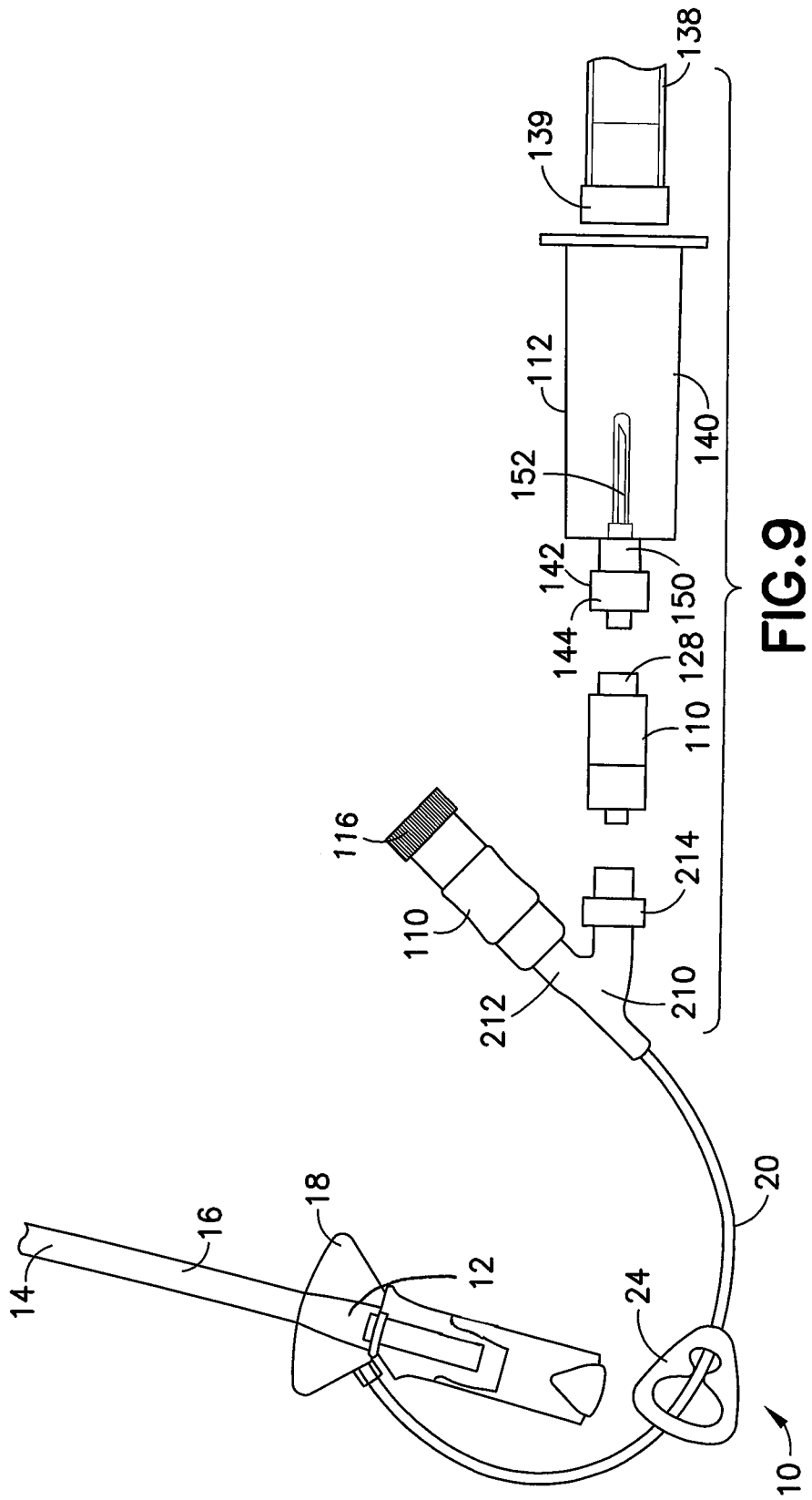
FIG. 9 is a perspective view of the assembly of FIG. 8 with the side port, sampling device, and collection device detached from one another.
Figure 10:
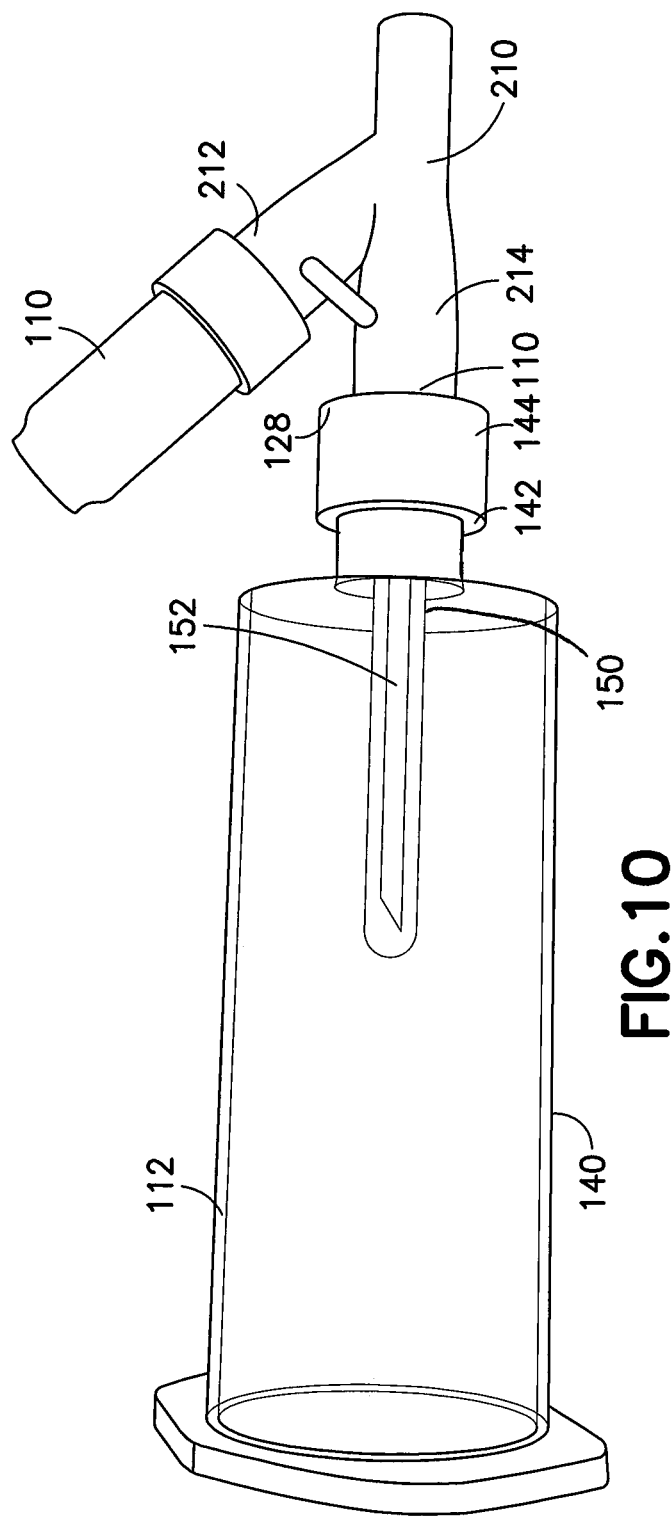
FIG. 10 is a side view of the side port, sampling device, and collection device of FIG. 8.

With reference now to FIGS. 8-10, a further embodiment of an extravascular system 10 including the vascular access device 12 having a through-portion 210 and a side port 212 is depicted. The through portion 210 includes a main outflow port 214 in addition to the side port 212. The main outflow port 214 and/or the side port 212 may include female luer lock connections configured to receive a corresponding narrow tubular portion 120 of a blood sampling device 110, as is depicted in FIG. 8.

By including a blood sampling device 110 in each of the main outflow port 214 and the side port 212, blood samples may be collected for different types of testing and analysis. For example, the sampling devices 110 may be configured to collect different volumes of blood. Alternatively, one blood sampling device 110 may include a preservative or anti-coagulant for modifying the composition of the collected blood while the second sampling device 110 may not include any such chemical components. In certain embodiments, the side port 212 may be used to access a blood sample which the blood sampling device remains connected to the adapter and the vascular access device.

In one non-limiting embodiment, the sampling device 110, which is free of preservative chemicals, may be connected to the sample container collection device 112. In this configuration, a blood sample having a preservative for point-of-care testing, a blood sample without a preservative for additional point-of-care testing, and a blood sample contained within a sample container 138 for conventional laboratory testing may be collected at the same time through the same vascular access device 12. There is no need for additional finger pricks or needle insertions to obtain the required samples from the patient. In certain embodiments, the sampling devices 110 may be color coded so that a user can easily distinguish which sampling device 110 includes additional preserving chemicals and which sampling device does not.

Figure 11:
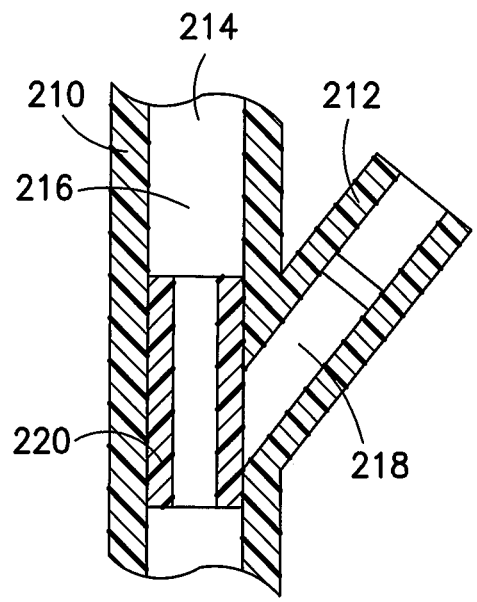
FIG. 11 is a cross-sectional view of the side port of FIG. 8.
Figure 12:
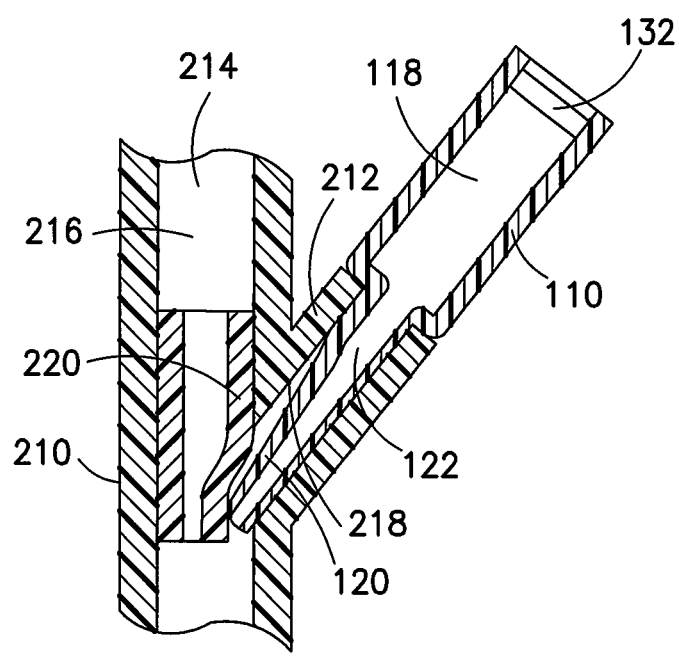
FIG. 12 is a cross-sectional view of the side port of FIG. 8 with the sampling device extending therefrom.

With reference to FIGS. 11 and 12, cross sectional views of the blood sampling device 110 having a through portion 210 and sampling device 110 are depicted. The through portion 210 includes a main lumen 216 extending from the luer access adapter 22 of the main outflow port 214 and the blood sampling device 110 also includes a side lumen 218 extending to the side outflow port 212. The device may further include an internal transitionable valve 220. As shown in FIG. 11, the valve 220 is configured so that in the unbiased, closed position, fluid flow through the main lumen 216 from the luer access adapter 22 to the main outflow port 214 is permitted; fluid flow through the side lumen 218 to the side port 212 is prevented. This configuration permits blood to flow directly to the sample container collection device 112 so that sample containers 138 may be filled easily and, if necessary, continuously. As shown in FIG. 12, the valve 220 is transitioned to a second position when the narrow tubular portion 120 and access lumen 122 of the sampling device 110 are inserted into the side port 212. More specifically, the narrow tubular portion 120 contacts a portion of the valve 220 and pushes the valve 220 out of the way. When the valve 220 is pushed out of the way, fluid communication between the main lumen 216 and side lumen 218 is established thereby permitting the sampling device 110, inserted through the side port 212, to fill with blood for testing.

With reference to FIG. 13, a further embodiment of the extravascular system 10 is depicted including both the main outflow port 214 and the side port 212 connected to sampling devices 110 with end caps 116 affixed thereto. The sampling devices 110 are not connected to a sample container collection device 112 as was depicted in FIG. 8. In this configuration, the sampling devices 110 can be filled and used for different testing and analysis procedures. As described above, one sampling device 110 may include a preservative chemical and the other may not. The sampling devices 110 may be color coded to clarify which sampling device is intended for use in which testing or analysis procedure.

Having described the components of the blood sampling device 110, sample container collection device 112, and various configurations for extravascular systems 10, a method of collecting a blood sample using an extravascular system 10 will now be described. A clinician establishes a vascular access site on a patient using any known means for establishing such access such as a needle 14, catheter 16, or blood collection set as is known in the art. The needle 14 and/or catheter 16 may include a shielding structure 18 for shielding a user from the needle 14 as well as other safety structures as are known in the art. Extension tubing 20 is connected to the vascular access device 12 and extends from the vascular access site to an open end of the tube having a port or luer access adapter 22. The luer access adapter 22 may include a valve or septum 156 to prevent flow of fluid from the access site when the luer access adapter 22 is not connected to another device. Alternatively, the tubing may have a flow restrictor, such as a clamp 24, which can be manually transitioned from a fluid allowing a position in which fluid flow is restricted. The clinician can transition the clamp 24 as necessary to perform the desired procedure.

Once the vascular access device 12 is in place, the clinician inserts the narrow tubular portion 120 of the sampling device 110 into the female luer access adapter 22 of the vascular access device 12 to establish fluid communication between the vascular access device 12 and sampling device 110. In certain configurations, the sampling device 110 is provided with the vented end cap 116 already attached. As blood is drawn into the extravascular system 10, air within the system is vented through the end cap 116, thereby drawing blood toward the sampling device 110. Alternatively, the sampling device 110 may be provided with a sample container collection device 112 attached thereto. In that case, air is vented through the sampling device 110 and exits the extravascular system 10 through the needle cannula 152 of the collection device 112.

If a collection device 112 is connected to the extravascular system 10, the clinician will permit blood to flow through the sampling device 110 and into the sample container 138. When the container 138 is filled with a desired amount of blood, the sample container 138 is removed from the collection device 112. Removing the sample collection container 138 causes the septum 156 of the collection device 112 to seal, thereby preventing further flow of blood through the needle cannula 152. The clinician may insert additional sample containers 138 on the collection device 112 to collect additional blood samples. Once the required number of sample containers 138 is filled, the septum 156 is closed and blood collects in the reservoir 118 of the sampling device 110.

Figure 14:
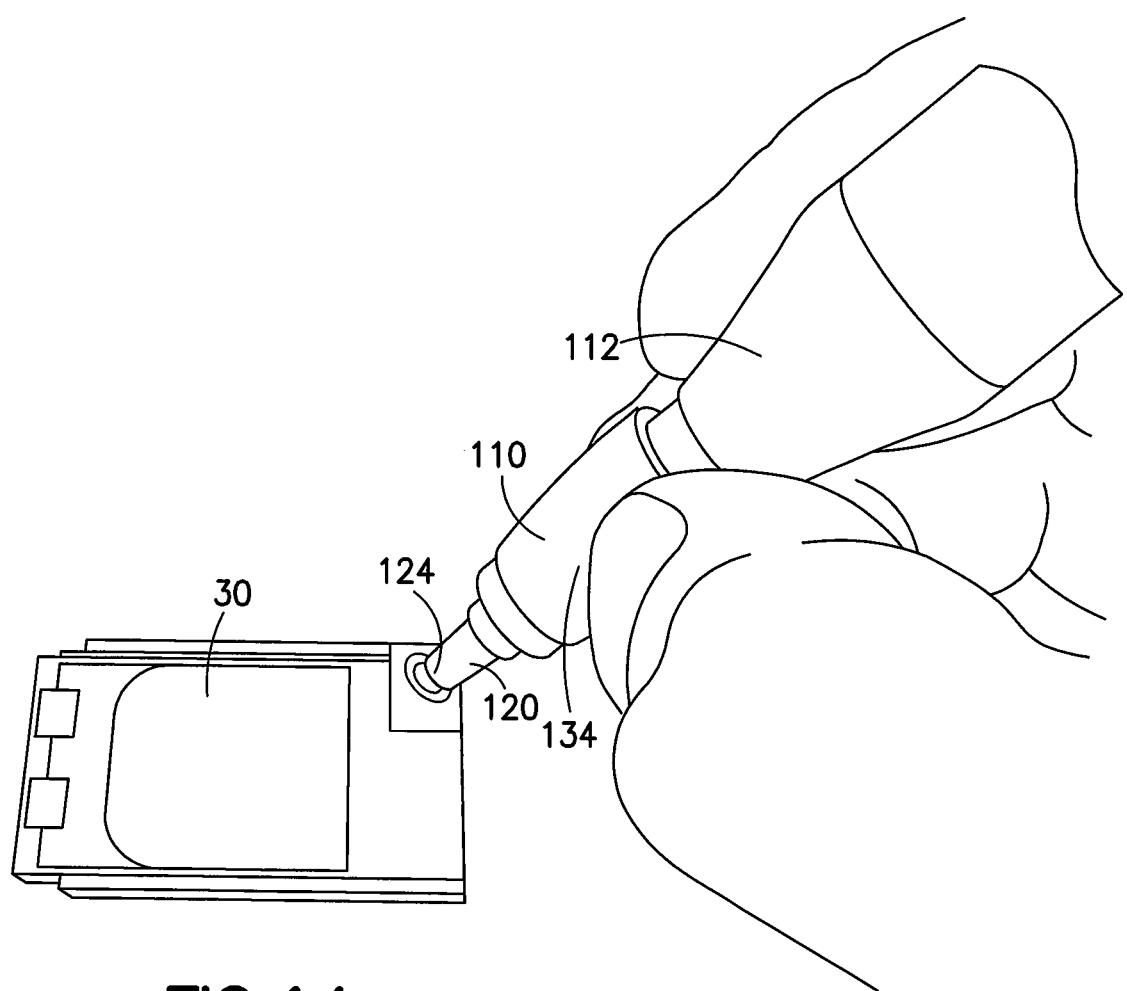
FIG. 14 is a schematic perspective view of a user dispensing a biological fluid from the sampling device of FIG. 1, to a testing apparatus, in accordance with an embodiment of the present invention.

In either of the above described configurations, the next step is removing the sampling device 110 from the vascular access device 12. In certain configurations, before removing the sampling device 110, the clinician must close the flow restrictor or clamp 24 to prevent additional fluid flow through the extension tubing 20. Alternatively, the female luer access adapter 22 may include an automatically closeable valve or septum 156 which closes to prevent further fluid flow through the extravascular system 10. When the sampling device 110 is removed from the female luer access adapter 22, blood is retained within the reservoir 118 of the sampling device 110 by the surface tension of the blood relative to the inner peripheral wall of the access lumen 122. The clinician then moves the sampling device 110 to a point-of-care testing device 30 such as a test strip. As is shown in FIG. 14, the clinician compresses the sampling device 110 causing the compressible portion 134 to deflect inwardly toward the reservoir 118, thereby reducing the inner volume of the reservoir 118 and increasing the fluid pressure within the reservoir 118. When a specific internal fluid pressure is reached, a portion of the blood contained in the reservoir 118 is ejected from the reservoir 118 through the access lumen 122 and narrow tubular portion 120 of the sampling device 110. The ejected blood is permitted to collect on the test strip or within the diagnostic testing cartridge. The clinician may then analyze the blood sample using the point-of-care testing device 30 and record relevant results for further analysis.

The present blood sampling device 110, extravascular system 10, and method of use thereof, significantly reduces the number of components required in order to obtain a diagnostic blood sample following vascular access using an IV or similar blood collection set. As described herein, embodiments of the blood sampling device 110, specimen container collection device 112, and extravascular system 10 may be used to obtain, prepare, and directly test blood samples during normal process of venous access. The extravascular system 10 may also be used to fill a standard sample container 138 to send to a laboratory for traditional testing. These embodiments facilitate the entire blood sampling process for clinicians by reducing the number of process steps and reducing the amount of time between sampling and obtaining test results.

As discussed hereinabove, various point-of-care testing devices 30 are known in the art. Such point-of-care testing devices 30 include test strips, glass slides, diagnostic cartridges, or other testing devices for testing and analysis. Test strips, glass slides, and diagnostic cartridges are point-of-care testing devices 30 that receive a blood sample and test that blood for one or more physiological and biochemical states. There are many point-of-care devices 30 that use cartridge based architecture to analyze very small amounts of blood bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A biological fluid sampling device engageable with a separate vascular access device, comprising:

a housing enclosing a biological fluid reservoir;

an access lumen in fluid communication with the separate vascular access device and the reservoir;

an outflow lumen having a first end provided in fluid communication with the reservoir and a second end; and a vented cap disposed over the second end of the outflow lumen and comprising:

a gas permeable vent in gaseous communication between the reservoir and an ambient environment; and a channel in fluid communication with the outflow lumen and positioned between the vent and the reservoir;

wherein the housing comprises a compressible portion, wherein compression of the compressible portion expels the fluid sample from the reservoir through the access lumen.

2. The biological fluid sampling device of claim 1, further comprising a luer lock at least partially surrounding the access lumen.

3. The biological fluid sampling device of claim 1, wherein the vented cap comprises a luer lock for insertion in the outflow lumen.

4. The biological fluid sampling device of claim 3, wherein the vented cap comprises a fastener for removably connecting a portion of the cap to a portion of the housing.

5. The biological fluid sampling device of claim 1, wherein the compressible portion comprises a plurality of gripping members.

6. The biological fluid sampling device of claim 1, wherein the reservoir contains a sample stabilizer.

7. The biological fluid sampling device of claim 1, wherein the reservoir comprises a plurality of chambers.

8. The biological fluid sampling device of claim 7, wherein the housing comprises a plurality of compressible portions, each of the plurality of compressible portions corresponding to one of the plurality of chambers, and wherein compression of one of the compressible portions expels the fluid sample from the corresponding chamber through the access lumen.

9. The biological fluid sampling device of claim 7, wherein each of the plurality of chambers comprises a sample stabilizer.

10. The biological fluid sampling device of claim 7, wherein each of the plurality of chambers is configured to hold a different volume.

11. A biological fluid sampling and collection assembly comprising:
a biological fluid sampling device comprising:
a housing enclosing a biological fluid reservoir;
an access lumen in fluid communication with a separate vascular access device and the reservoir; and
an outflow lumen having a first end provided in fluid communication with the reservoir and a second end; and
a vented cap disposed over the second end of the outflow lumen, the vented cap comprising:
a gas permeable vent in gaseous communication between the reservoir and an ambient environment; and
a channel in fluid communication with the outflow lumen and positioned between the vent and the reservoir; and
a sample collection device comprising:
an adapter for accessing an interior of a sample container and for establishing fluid communication between the biological fluid reservoir and an interior of the sample container, thereby allowing fluid communication between the biological fluid reservoir and the interior of the sample container; and
a flow restrictor engaged with the adapter, the flow restrictor transitionable from an open position, in which fluid communication is permitted between the biological fluid reservoir and the interior of the sample container, to a closed position, in which the biological fluid reservoir is in fluid isolation from the interior of the sample container.

12. The biological fluid sampling and collection assembly of claim 11, wherein the biological fluid reservoir contains a fluid and, wherein when the flow restrictor is in the open position, the fluid passes from the biological fluid reservoir to the interior of the sample container.

13. The biological fluid sampling and collection assembly of claim 11, wherein the flow restrictor is in the open position when the sample container is engaged with the adapter, and wherein the flow restrictor is in the closed position when the sample container is removed from the adapter.

14. The biological fluid sampling and collection assembly of claim 11, wherein the sample container is a vacuum evacuated container.

15. The biological fluid sampling and collection assembly of claim 11, further comprising the separate vascular access device in fluid communication with the access lumen.

16. The biological fluid sampling and collection assembly of claim 15, further comprising an adapter connected between the separate vascular access device and the biological fluid sampling device.

17. The biological fluid sampling and collection assembly of claim 16, wherein the adapter comprises:
a housing;
a main lumen enclosed within the housing having a main outflow port;
a side port including a side lumen extending from and in fluid communication with the main lumen; and
a valve transitionable from a first position in which fluid flow is permitted through the main lumen and fluid flow is prevented through the side lumen, to a second position in which fluid flow through both the main lumen and side lumen is permitted.

18. The biological fluid sampling and collection assembly of claim 17, wherein the valve is transitioned from the first position to the second position by insertion of a tubular member into the side lumen through the side port.

19. The biological fluid sampling and collection assembly of claim 11, wherein the biological fluid reservoir contains a sample stabilizer.

* * * * *